United States Patent [19]

Lotsof

[11] Patent Number: 4,499,096

[45] Date of Patent: Feb. 12, 1985

[54] RAPID METHOD FOR INTERRUPTING THE NARCOTIC ADDICTION SYNDROME

[76] Inventor: Howard S. Lotsof, 330 Stanley Ave., Staten Island, N.Y. 10301

[21] Appl. No.: 553,138

[22] Filed: Nov. 18, 1983

[51] Int. Cl.³ .................. A61K 31/435; A61K 31/475
[52] U.S. Cl. ................................. 514/214; 514/812
[58] Field of Search .............................. 424/262, 256

[56]  References Cited
PUBLICATIONS

Merck Index, 9th Ed. (1976), p. 650.

*Primary Examiner*—Stanley J. Friedman
*Attorney, Agent, or Firm*—Howard C. Miskin

[57] ABSTRACT

The administration to a heroin addict of ibogaine, ibogaine HCl or other non toxic salts of ibogaine, an alkaloid of the family apocynaceae, has been discovered to unexpectedly interrupt the physiological and psychological aspects of the opiate addiction syndrome. A single treatment was effective for about 6 months, and a series of 4 treatments was effective for approximately 3 years. The treatments consisted of the oral administration of ibogaine or its salts in dosage ranges of 6 mg/kg to 19 mg/kg. The minimum effective dose was 400 mgs and dosage increases above 1000 mgs were found to be unnecessary. Treatments were effective in 71% of the cases.

11 Claims, No Drawings

RAPID METHOD FOR INTERRUPTING THE NARCOTIC ADDICTION SYNDROME

BACKGROUND OF THE INVENTION

The present invention relates generally to improvements in the treatment of opiate addiction and it relates particularly to an improved method for interrupting the physiological and psychological aspects of the heroin addiction syndrome.

Many procedures and regimes have heretofore been employed and proposed for the treatment of opiate addiction, but these, particularly when applied to heroin addiction, possess numerous drawbacks and disadvantages. The treatments are long, usually very painful and uncomfortable, frequently unreliable and accompanied by highly undesirable side effects and commonly initiate other addictions. Thus the conventional and heretofore proposed treatments for heroin addiction leave much to be desired.

HISTORICAL BACKGROUND

Ibogaine is one of at least 12 alkaloids found in the *Tabernanthe iboga* shrub of West Africa. The indigenous peoples have used the drug as a ritual, ordeal or initiation potion in large dosages and as a stimulant in smaller doses. One of the first European references to the drug was made by Professor Baillon at the Mar. 6th, 1889 session of the Linnaen Society in Paris during which he described samples obtained by Griffon de Bellay from Gabon and the French Congo.

Early isolation and identification of ibogaine was accomplished by Dybowski and Landrin (Compt. rend. ac. sc. 133:748, 1901); Haller and Heckel (ibid. 133:850); Lambert and Heckel (ibid. 133:1236) and Landrin (Bull. sc. pharm. 11:1905).

Interest in the drug seemed to lie fallow until it was picked up by Raymond-Hamet and his associates. Rothlin, E. and Raymond-Hamet published the "Effect of Ibogaine on the Isolated Rabbit Uterus" in 1938 (Compt. rend. soc. biol. 127:592-4). Raymond-Hamet continued to study the drug for a period of 22 years. He singularly published 9 papers: Pharmacological Action of Ibogaine (Arch. intern. pharmacodynamie, 63:27-39, 1939), Two Physiological Properties Common to Ibogaine And Cocaine (Compt. rend. soc. biol. 133:426-9, 1940), Ibogaine And Ephedrine (Ibid. 134:541-4, 1940), Difference Between Physiological Action of Ibogaine And That of Cocaine (Ibid. 211:285-8, 1940), Mediate And Intermediate Effects Of Ibogaine On The Intestine (Compt. rend. soc. biol. 135 176-79, 1941), Pharmacologic Antagonism Of Ibogaine (Compt. rend.. 212: 768-771, 1941), Some Color Reactions Of Ibogaine (Bull. soc. chim. Biol., 25: 205-10, 1943), Sympathicosthenic Action Of Ibogaine On The Vessels Of The Dog's Paw (Compt. rend. 223: 757-58, 1946), and Interpretation Of The Ultraviolet Absorption Curves Of Ibogaine And Tabernanthine (Ibid. 229: 1359-61, 1949).

Vincent, D. began his work on ibogaine by a collaboration with Sero, I.: Inhibiting Action Of Tabernanthe Iboga On Serum Cholinestearase (Compt. rend. Soc. Biol. 136: 612-14, 1942). Vincent participated in the publication of five other papers: The Ultraviolet Absorption Spectrum Of Ibogaine (Brustier, B., Vincent, D., & Sero, I., (Compt. rend., 216: 909-11, 1943), Detection of Cholinesterase Inhibiting Alkaloids (Vincent, D. and Beaujard, P., Ann. pharm. franc. 3: 22-26, 1945), The Cholinesterase Of The Pancreas: Its Behavior In the Presence Of Some Inhibitors In Comparison With The Cholinesterases of Serum And Brain (Vincent, D. and Lagreu, P., Bull. soc. chim. biol. 31: 1043-45, 1949); and two papers, which he and Raymond-Hamet worked on together: Action Of Some Sympathicosthenic Alkaloids On the Cholinesterases (Compt. rend. soc. biol., 150: 1384-1386, 1956) and On Some Pharmacological Effects Of Three Alkaloids Of Tabernanthe Iboga, Baillon: Ibogamine, Iboluteine And Tabernanthine (Compt. rend. soc. biol., 154: 2223-2227, 1960).

The structure of ibogaine was investigated by Dickel et al. (J.A.C.S. 80, 123, 1958). The first total synthesis was cited by Buchi et al. (J.A.C.S. 87, 2073, 1965) and (J.A.C.S. 88, 3099, 1966).

In 1956 Salmoiraghi and Page elucidated ibogaine's relations to serotonin (J. Pharm & expt. ther. 120 (1), 20–25, 1957.9). About the same time J. A. Schneider published three important papers. The first, Potentiation Action Of Ibogaine On Morphine Analgesia was done in collaboration with Marie McArthur (Experentia 12: 323-324, 1956). The second was Neuropharmacological Studies of Ibogaine: An Indole Alkaloid With Central-Stimulant Properties (Schneider, J. A. and Sigg, E. B., Annals of N.Y. acad. of sciences, Vol 66: 765-776, 1957) and third was An Analysis Of The Cardiovascular Action Of Ibogaine HCl (Schneider, J. A. & Rinehard, R. K., Arch. int. pharmacodyn., 110: 92-102, 1957).

Ibogaine's stimulant properties were further investigated by Chen and Bohner in A Study Of Central Nervous System Stimulants (J. Pharm. and Expt. Ther., 123 (3): 212-215, 1958). Gershon and Lang published A Psychological Study Of Some Indole Alkaloids (Arch. intern. pharmacodynamie, 135: 31-56, 1962).

In 1969, Claudio Naranajo reported on the effects of both ibogaine and harmine on human subjects in his paper: Psychotherapeutic Possibilities Of New Fantasy-Enhancing Drugs (Clinical Toxicology, 2 (2): 209–224, June 1969).

Dhahir, H. I., as his 1971 doctoral thesis, published A Comparative Study Of The Toxicity of Ibogaine And Serotonin (University Microfilm International 71-25-341, Ann Arbor, Mich.). The paper gives an overview of much of the work accomplished with ibogaine.

Additional studies of interest include: The Effects Of Some Hallucinogens On Aggressiveness Of Mice and Rats (Kostowski et al., Pharmacology 7: 259–263, 1972). Cerebral Pharmacokinetics Of Tremor-Producing Harmala And Iboga Alkaloids (Zetler et al., Pharmacology 7 (4): 237–248, 1972), High Affinity 3H-Serotonin Binding To Caudate: Inhibition By Hallucinogens And Serotonergic Drugs (Whitaker, P. and Seeman, P., Psychopharmacology 59: 1–5, 1978, Biochemistry), Selective Labeling Of Serotonin Receptors by d-(3H) Lysergic Acid Diethylamide In Calf Caudate (Proc. natl. acad. sci., USA, Vol. 75, No. 12, 5783–5787, Dec. 1978, Biochemistry) and A Common Mechanism Of Lysergic Acid, Indolealkylamine And Phenthylamine Hallucinogens: Serotonergic Mediation Of Behavioral Effects In Rats (Sloviter, Robert et al, J. Pharm. & Expt. Ther., 214 (2): 231–238, 1980).

SUMMARY OF THE INVENTION

It is a principal object of the present invention to provide an improved method for the treatment of opiate addiction.

Another object of the present invention is to provide an improved method for interrupting the physiological and psychological aspects of the heroin addiction syndrome.

Still another object of the present invention is to provide a method of the above nature characterized by its high degree of success, the absence of the great pain and discomfort accompanying earlier treatments, the ease and convenience of application the absence of undesirable or persistent side effects and the persistent effectiveness of the treatment.

The above and other objects of the present invention will become apparent from a reading of the following decription which sets forth preferred embodiments thereof.

A feature of the present invention is based on the discovery that an alkaloid of the family Apocynaceae and its therapeutically active derivatives and salts, particularly, ibogaine and its therapeutically active, non-toxic derivatives and salts for example, ibogaine hydrochloride and other non-toxic salts of ibogaine, possess the unexpected unique ability to disrupt the heroin addiction syndrome. Examples of other salts of ibogaine which may be used are ibogaine hydrobromide, and any other non-toxic salt of ibogaine.

For the purpose of definition, the heroin addiction syndrome is meant to consist of all the symptomology demonstrated by addicts in their use of and search for heroin. The interruption of the syndrome was accomplished in five out of seven (71%) of the test subjects who were addicted to heroin. None of the test subjects were seeking to terminate their habits, and all seven were enamored with narcotics.

A single treatment with ibogaine or ibogaine HCl of doses ranging from 6 mg/kg to 19 mg/kg administered orally, disrupted the subject's use of heroin for about six months.

A treatment lasts about thirty hours during which time ibogaine exerts a stimulant effect. Apparently, an abreactive process is involved during ibogaine therapy but is not noticeable until the patient wakes from natural sleep occurring after primary and secondary effects of ibogaine are diminished. When effective, ibogaine left the addict with no desire to use heroin and no noticeable signs of physical withdrawal. Subjects appeared relaxed, coherent, with a sense of direction and feelings of confidence.

Ibogaine was one of five substances we studied. The other four—mescaline, psilocybin, LSD and DMT though different in duration of action and intensity—have similar psychotropic effects that are well documented and will not be discussed here. Ibogaine, unlike the others, is not a euphoriant hallucinogen and did not leave the subjects open to swells of emotion. While under the influence of ibogaine, emotional responses to traumatic repressed thoughts and feelings appeared to be negated.

Another effect of ibogaine administration that was found interesting was that even after twenty-six to thirty hours of wakefulness, subjects slept three to four hours and awoke fully rested. This pattern continued, diminishing slowly, over a three to four month period.

The effects of oral administration of ibogaine are first noticed in fifteen to twenty minutes. Initially, a numbing of the skin is accompanied by an auditory buzzing or oscillating sound. Within twenty-five to thirty-five minutes the auditory transcends across the sensory mechanisms to include the visual: objects appear to vibrate with great intensity. It is at this time that the dream enhancement or hallucinatory effects begin. In many cases an acute stage of nausea follows the hallucinatory phase. The visions end abruptly and the numbness of the skin begins to abate.

This is followed by six to eight hours of a high energy state during which the subjects see "lightening" or flashes of light dance about them. Thoughts which seem to amplify the meaning of the visions seen during the primary phase of ibogaine intoxication continue during this period.

Between twenty-six and thirty-six hours, the level of stimulation diminishes and the test subject falls asleep.

Thus, three stages of ibogaine intoxication have been observed. First, an hallucinatory period lasting for three to four hours during which time the person receiving ibogaine manifests repressed material visually. Second, a high energy period accompanied by flashes of light, the appearance of a vibration to all objects, and the awareness of thoughts appropriate to the visual material seen by the subject. Third, a diminishing energy period free of vibration or light flashes and culminating in sleep.

In the administration of acceptable dosage forms, any one of a variety of preparations may be compounded, for example: capsules, tablets, pills, powders, solutions, etc. In addition to the active agent, there may be present additional substances used in the manufacture of pharmaceutical preparations such as binders, fillers and other inert ingredients.

DESCRIPTION OF THE PREFERRED EMBODIMENTS

The following examples are given merely by way of illustration and are not intended to limit the scope of the present invention.

EXAMPLE 1

Male, age 19, weight 143 lbs. Drug use consists of one, five-dollar bag of heroin, divided into four doses and injected intravenously over a two day period. This rate of drug use had been consistent for three weeks and followed a two month phase of intermittent use. This subject was the only addict to receive a planned series of treatments.

The first treatment consisted of 400 mg of ibogaine HCl by oral administration. This curtailed heroin use for six months. At that time a series of treatments was initiated. The series consisted of an ibogaine treatment every seven days. The first dose was 500 mg ibogaine by oral administration. The second was 500 mg plus 250 mg fifteen minutes later, the third was 600 mg and a final dose of 1000 mg.

The treatment series was considered complete when the hallucinatory stage failed to make itself evident. The subject remained heroin free for 3 years, and had no further desire to take ibogaine for 18 months.

EXAMPLE 2

Male, age 22, weight 110 lbs. Drug use had persisted for eighteen months and had reached a level of fifteen three-dollar bags of heroin a day. A single dose of 400 mg of ibogaine HCl resulted in an interruption of the addiction syndrome for six months.

EXAMPLE 3

Male, age 20, weight 135 lbs. Drug use by this subject had been intermittent for six months, and subject was currently using one or two three-dollar bags of heroin a day. A single 500 mg dose resulted in the subject remaining heroin free for six and a half months.

EXAMPLE 4

The only female addict in this study was 23 years old and weighed 95 lbs. Intermittent heroin use for one year and current use of two to three three-dollar bags of heroin a day. A single 500 mg dose resulted in curtailed heroin use for at least 6 months, after which time we lost contact with this subject.

EXAMPLE 5

The subject was 25 years of age and weighed 115 lbs. Drug use consisted of one or two, five-dollar bags of heroin a day for three months. A single dose of 500 mg ibogaine was administered orally. The visual phase was not elicited in this patient, but a break in heroin use of four weeks occurred.

Six months later, when additional ibogaine was available, the subject was given another 500 mg. At that time the subject had reduced his heroin intake to two, three-dollar bags a day. This second dose of 500 mg of ibogaine also failed to allow the subject to undergo the dream enhancement phase of ibogaine treatment but, nevertheless, resulted in an interruption of heroin use. One week later the subject was given 1000 mg of ibogaine HCl by oral administration. A thousand milligrams was the maximum dose which we felt to be comfortable for the addict. The patient responded well and experienced the visual stages of ibogaine ingestion for the first time. Heroin use stopped for five and a half months.

MODE OF ACTION

There are a number of mechanisms and relationships of action by which ibogaine may interrupt the heroin addiction syndrome. These include memory coding by RNA and protein, immune mechanisms, neurohormonal adaptations, involvement in systems including catecholamines, acetylcholine, serotonin, adrenergic compounds, hypothalmic-pituitary neuro-hormones, opiate receptors outside the CNS as well as adaptations taking place outside the central nervous system. The mode of action may also include structure-activity relationships, receptors within the brain or other binding sites, psychological causes, systems involving endorphins, metabolic imbalances, prevention of access of drugs to the site of action, or occupation and saturation of receptor sites.

While the exact mechanism or mechanisms of action by which ibogaine interrupts the heroin addiction syndrome is not clear, it is known that it functions by interaction with one or more of the above systems. It is not intended, however, that the present invention be limited to any particular theory or mechanism of action.

The advantage of this invention is that it allows for the rapid interruption of physiological and psychological withdrawal and the elimination of the subject's desire to use heroin for about six months. The invention itself is non-addicting, and in a series of treatments will remove its own potential for abuse.

While there have been described preferred embodiments of the present invention it is apparent that numerous alterations, omissions and additions may be made without departing from the spirit thereof.

I claim:

1. The method of treating heroin addiction comprising administering internally to the addict a dosage of between 6 mg and 19 mg per kg weight of the addict of ibogaine or a therapeutically active compound thereof or a mixture thereof.

2. The method of claim 1 wherein said dosage is orally administered.

3. The method of claim 2 wherein said administered dosage is ibogaine or a non-toxic salt thereof or a mixture thereof.

4. The method of claim 3 wherein said administered dosage is of a weight of between 400 mg and 1000 mg.

5. The method of claim 1 wherein a plurality of said dosages are administered, the administration of successive dosages being separated by a plurality of days.

6. The method of claim 1 wherein said dosage is the hydrochloride or hydrobromide salt ibogaine.

7. The method of treating heroin addiction comprising orally administering to the addict between 6 mg and 19 mg per kg of weight of the addict ibogaine or the hydrochloride or hydrobromide compound thereof or mixtures thereof.

8. The method of claim 7 wherein the administered dosage is between 400 mg and 1000 mg.

9. The method of claim 7 or 8, wherein a plurality of said dosages are administered, the administration of successive dosages being separated by a plurality of days.

10. The method of claim 7 wherein said dosage is in capsule tablet, pill, powder, or solution form.

11. The method of claim 7 wherein said dosage is admixed with binders, fillers, or other inert ingredients.

* * * * *